United States Patent [19]

Kerry et al.

[11] Patent Number: 4,517,201

[45] Date of Patent: May 14, 1985

[54] SYNERGISTIC COMPOSITIONS AND METHODS OF COMBATING INSECTS EMPLOYING AMITRAZ AND CYPERMETHRIN

[75] Inventors: John C. Kerry, Edwalton; David M. Weighton, Saffron Walden, both of England

[73] Assignee: FBC Limited, Cambridge, England

[21] Appl. No.: 516,455

[22] Filed: Jul. 22, 1983

Related U.S. Application Data

[63] Continuation-in-part of Ser. No. 305,211, Sep. 24, 1981, abandoned, which is a continuation-in-part of Ser. No. 172,392, Jul. 25, 1980, abandoned, which is a continuation of Ser. No. 920,155, Jun. 29, 1978, abandoned.

[30] Foreign Application Priority Data

Jul. 1, 1977 [GB] United Kingdom ............... 27536/77

[51] Int. Cl.$^3$ ..................... A01N 33/02; A01N 37/34
[52] U.S. Cl. .................................................... 514/521
[58] Field of Search ................................ 424/304, 330

[56] References Cited

FOREIGN PATENT DOCUMENTS 1327935  8/1973  United Kingdom ................ 424/330
1413491 11/1975  United Kingdom ................ 424/305

Primary Examiner—Allen J. Robinson
Attorney, Agent, or Firm—Gordon W. Hueschen

[57] ABSTRACT

Pesticidal compositions containing amitraz and the synthetic pyrethroid cypermethrin are described. The compositions which preferably contain the active ingredients in a ratio of from 250:1 to 1:10 by weight, are synergistic and have activity against a wide range of insect and acarid pests. They are particularly useful in controlling pests on cotton and fruit crops.

7 Claims, No Drawings

SYNERGISTIC COMPOSITIONS AND METHODS OF COMBATING INSECTS EMPLOYING AMITRAZ AND CYPERMETHRIN

This application is a continuation in part of application Ser. No. 305,211 filed Sept. 24, 1981, now abandoned, which itself is a continuation in part of application Ser. No. 172,392 filed July 25, 1980, now abandoned, which itself is a continuation of application Ser. No. 920,155 filed June 29, 1978, now abandoned.

This invention relates to pesticidal compositions and methods of controlling pests.

A slow deterioration in the efficacy of pesticides employed to protect crops and animal health is often observed as pests develop resistance to them. In consequence there is always a need for new pesticides which restore activity and which, moreover, can be used to combat a wide spectrum of pests.

We have now discovered that mixtures of the pesticide, amitraz, with synthetic pyrethroids have valuable and unexpected properties. For example in the context of certain pests which attack crops we have observed that the pesticidal activity of the mixtures is greater than would be expected and synergism is exhibited.

Accordingly the invention provides a pesticidal composition comprising amitraz and the synthetic pyrethroid cypermethrin. Preferably the components are present in a ratio of between 250:1 to 1:10, preferably between 100:1 to 1:5, e.g. 50:1 to 1:1, and especially from 25:1 to 4:1 by weight.

Amitraz is 1,5-di-(2,4-xylyl)-3-methyl-1,3,5-triazpenta-1,4-diene and cypermethrin is (RS)-alpha-cyano-3-phenoxybenzyl (IRS)-cis, trans-3-(2,2-dichlorovinyl)-2,2-dimethylcyclopropanecarboxylate.

The mixtures of the invention are active against a wide range of pests, both insects and acarids, and one of their advantages stems from the fact that they can be applied to a crop attacked by pests at all stages of their life cycle. This is an important advantage since the timing of pesticide application is made less critical and there is a greater chance of obtaining good, overall, control of the pests in a single treatment. In addition to their synergistic activity we have observed an extension to the spectrum of control of resistant pests. Amongst the pests the mixtures are effective against are insects such as the diamond back moth *Plutella xylostella*; aphids for example the green peach aphid *Myzus persicae*; codling moth *Cydia pomonella*; cabbage white butterfly *Pieris brassicae*; pear psylla *Psylla pyri*; boll weevil *Anthonomis grandis*; and noctuid insects such as for example the tobacco budworm *Heliothis viriscens*, the bollworm *Heliothis zea*, pink bollworm *Pectinophora gossypiella* and cotton leaf worm *Spodoptera littoralis*; and acarids (pests of the order Acarina) such as for example spider mites *Tetranychus urticae, Tetranychus citri, Panonychus citri* and *Panonychus ulmi*. These pests attack many important crops and in doing so cause great economic damage. Thus the mixtures find application on cotton, maize and soybean crops, soft fruit and top fruit such as apple pear, peach and citrus crops. In addition to their extensive use in the treatment of crops the mixtures can be used to control ectoparasites on animals.

It is, of course, possible to obtain the advantage of the invention by use of more than one synthetic pyrethroid in admixture with amitraz or by the addition of other pesticides which do not affect synergistic co-operation with amitraz.

The compositions of the invention can be employed in a wide variety of forms and can comprise a liquid or solid diluent optionally together with a surface active agent. They are often most conveniently prepared in aqueous form immediately prior to use, for example, as a spray on pest-infested crops or animals. One such method is commonly called "tank mixing" in which the two, or more, pesticide ingredients in their commercially available forms are mixed together by the farmer in a quantity of water for direct application. The concentration of the active ingredients for application to a crop by conventional ground methods is preferably within the range of from 0.001 to 10 percent, especially from 0.005 to 5 percent by weight of the composition, but more concentrated compositions containing up to 20 percent by weight may be desirable in the case of aerial sprays. When an aqueous preparation is required for treatment of animals by means of, for example a spray race or dip the composition comprises an amount of active ingredients that is no-toxic to the host animal and is preferably from 0.002 to 1.0 percent, especially from 0.005 to 0.5 percent by weight of the composition.

The compositions of the invention include not only those in suitable form for direct application but also concentrated primary compositions which can be supplied to the user and which require dilution with a suitable quantity of water or other diluent before application. Such compositions may comprise a surface active agent in addition to the active ingredients and typical examples are an aqueous dispersion, an aqueous emulsion, an emulsifiable concentrate, a dispersible powder or a dusting powder. As a concentrated primary composition the concentration of active ingredients can vary widely and can be for example from 5 to 95 percent by weight of the composition.

An emulsifiable concentrate, also known as a 'miscible liquid', comprises a solution of the active ingredients in a water-immiscible solvent in association with one or more emulsifying agents. An emulsion formed when the emulsifiable concentrate is mixed with water.

A dispersible powder comprises the active ingredients in finely divided form in association with one or more dispersing agents so that a stable aqueous dispersion of the active ingredients is formed on mixing the powder with water. A finely divided inert solid diluent such as kaolin or celite is generally incorporated in the dispersible powder.

A dusting powder comprises the active ingredients intimately mixed with a solid pulverulent diluent, for example kaolin.

As a further aspect, the invention includes a method for controlling pests which comprises applying a composition comprising amitraz and cypermethrin to the locus of the pests, that is, the pests or their habitat. More particularly the invention comprises a method for protecting plants from insects and acarids by the use of such compositions and especially by employing any of the compositions described above, applied most conveniently as a foliar spray at a rate, for example, of from 0.25 to 6.0 kilograms per hectare.

A wide variety of crops including cotton, maize, soybeans, soft fruit and top fruit can be protected by treatment with the pesticidal composition of the invention. The method is of particular application to cotton crops and thus the invention includes a method for controlling insects on a cotton crop which comprises applying a composition of the invention to the locus of the insect. Some of the noctuid insects most harmful to cotton are bollworms, leaf worms and armyworms which can be controlled by application of the active ingredients preferably at a rate of from 0.25 to 5.0 kilograms per hectare, for example from 0.5 to 2.5 kilograms per hectare. More than one application of pesticide may often be desirable and when cotton crops are concerned, treatment at intervals of 3 to 30 days can be most suitable.

A further important application of the composition of the invention is in the control of pests on fruit crops such as vines, soft fruit such as for example raspberries, gooseberries, strawberries and red currants and top fruit such as for example apple, pear, peach and citrus crops. Thus the invention includes a method of controlling acarid and insect pests on a fruit crop which comprises applying a composition of the invention to the crop infested with pests. Some pests such as psyllid insects, codling moths and spider mites are an especially serious pest on top fruit such as apple, pear and peach crops and an aspect of the invention is the control of such pests on top fruit particularly by the application of compositions 1 to 3 referred to above. Application rates of the active ingredients are preferably within the range of from 0.25 to 5.0 kilograms per hectare, for example from 0.4 to 1.0 kilograms per hectare.

With regard to animal health uses, the invention includes a method for controlling pests harmful to domestic animals which comprises applying to the locus of the pest a composition of the invention. Sometimes it is convenient to spray the quarters in which an animal is kept in order to eliminate the pest from the animal's surroundings but more usually the animal is treated by external application either as a precaution against pest attack or in order to combat an infestation of pests. The method is especially applicable to animal livestock and to the control of insect or acarid ectoparasites which attach themselves to the external parts of the animal at some stage during their life cycle. For example ticks, mites, keds, lice and flies are amongst the pests which are a serious problem in the rearing of cattle, pigs and sheep. An especially preferred method is one for protecting cattle from cattle tick and other ectoparasites which comprises treating the cattle externally with a composition of the invention by means of, for example, a cattle dip, spray or 'pour-on' treatment.

The invention is illustrated by the following Examples.

EXAMPLE 1

The activity of pesticidal compositions against *Plutella xylostella* was tested according to the following procedure.

Ten larvae were placed in a tube together with a square inch of cabbage leaf which had been dipped in the test solution of amitraz, cypermethrin and mixtures of these two pesticides. After twenty-four hours untreated cabbage was added for food and after a further twenty-four hours an assessment was made of the mortality of the larvae.

The experiments were replicated twice and a percentage mortality calculated. It was found that amitraz at a rate of 100 ppm had no effect on the larvae but when mixed with cypermethrin increased the mortality as follows.

| Amitraz (ppm) | Cypermethrin (ppm) | Percentage mortality |
|---|---|---|
| 0 | 1 | 54 |
| 0 | 4 | 54 |
| 100 | 1 | 62 |
| 100 | 4 | 92 |

In a similar series of tests synergism was demonstrated as follows.

| Amitraz (ppm) | Cypermethrin (ppm) | Percentage mortality |
|---|---|---|
| 100 | 0 | 0 |
| 50 | 0 | 4 |
| 0 | 4 | 38 |
| 100 | 4 | 58 |
| 50 | 4 | 53 |

EXAMPLE 2

In another series of tests as described in Example 1 synergism was demonstrated as follows. Three replicates were used at each dose and from the data the $LD_{50}$s were calculated by probit analysis.

| Active ingredient | $LD_{50}$ (ppm) |
|---|---|
| Amitraz | 4137 |
| Cypermethrin | 6.07 |
| Amitraz/cypermethrin (4:1 mixture) | 13.9 |

The data were analysed by the method of Sun and Johnson (J. Econ. Entomol 1960 53, 887). In this method co-toxicity co-efficients of a mixture are determined by the equation.

$$\text{Co-toxicity} = \frac{\text{Actual Toxicity Index } (T.I)}{\text{Theoretical Toxicity Index } (T.I)} \times 100$$

A figure of greater than 100 indicates synergism. With the present data:

T.I. of amitraz against cypermethrin = 0.1467
T.I. of cypermethrin against cypermethrin = 100
Actual T.I. of 4:1 mixture against cypermethrin = 43.7

Theoretical T.I. of 4:1 mixture $= 0.1467 \frac{4}{5} + 100 \times \frac{1}{5} = 20.1$ Co-toxicity of 4:1 mixture $= \frac{\text{Actual T.I.}}{\text{Theoretical T.I.}} \times 100 = \frac{43.7}{20.1} \times 100 = 217$

What is claimed is:

1. An insecticidal composition comprising amitraz and the synthetic pyrethroid cypermethrin in a ratio of from 100:1 to 4:1 by weight.
2. An insecticidal composition according to claim 1 in which the ratio is from 25:1 to 4:1 by weight.
3. An insecticidal composition according to claim 1 in which the ratio is from about 100:1 to about 12.5:1 by weight.
4. An insecticidal composition in aqueous form suitable for direct application to a crop, comprising a composition as defined in claim 1 in which the concentration of active ingredients is from 0.005 to 5 percent by weight of the composition.
5. A method for controlling insects which comprises applying to the insects or their habitat an effective insect-controlling amount of a mixture of amitraz and the synthetic pyrethroid cypermethrin, wherein the ratio of Amitraz to cypermethrin is from 100:1 to 4:1 by weight.
6. The method of claim 5, wherein the ratio is from 25:1 to 4:1 by weight.
7. The method of claim 5, wherein the ratio is from about 100:1 to about 12.5:1 by weight.

* * * * *